United States Patent [19]

Rao

[11] Patent Number: 4,683,329
[45] Date of Patent: Jul. 28, 1987

[54] BENEFICIAL USE OF WATER IN CATALYTIC CONVERSION OF FORMAMIDES TO ISOCYANATES

[75] Inventor: Velliyur N. M. Rao, Wilmington, Del.

[73] Assignee: E. I. DuPont de Nemours and Company, Wilmington, Del.

[21] Appl. No.: 852,707

[22] Filed: Apr. 16, 1986

[51] Int. Cl.$^4$ .............................................. C07C 71/00
[52] U.S. Cl. .................................................... 560/338
[58] Field of Search ................................ 560/336, 338

[56] References Cited

U.S. PATENT DOCUMENTS

| | | | |
|---|---|---|---|
| 3,960,914 | 6/1976 | Lyons | 560/338 |
| 4,207,251 | 6/1980 | Heyboer | 560/338 |
| 4,537,726 | 8/1985 | Rao | 560/338 |

*Primary Examiner*—Alan Siegel
*Attorney, Agent, or Firm*—Craig H. Evans

[57] ABSTRACT

Water is fed together with formamide in vapor form in the production of isocyanates by silver-catalyzed oxidative dehydrogenation of formamides.

6 Claims, No Drawings

BENEFICIAL USE OF WATER IN CATALYTIC CONVERSION OF FORMAMIDES TO ISOCYANATES

BACKGROUND OF THE INVENTION

1. Technical Field

The present invention relates to processes for production of isocyanates by the metal-catalyzed reaction of formamides and oxygen.

2. Description of the Prior Art

Heyboer, U.S. Pat. No. 4,207,251, discloses a method for gas phase production of $C_{1-24}$ organo-isocyanates involving oxidative dehydrogenation of corresponding N-monosubstituted formamides. This reaction is extremely exothermic; therefore, some method for controlling reaction temperature must be employed to maintain reaction temperatures below those which would accelerate side reactions, or lead to decomposition of product isocyanates. For example, Heyboer discloses use of small diameter reactors, or introduction of large volumes of an inert gas to reaction mixtures to absorb liberated heat.

Rao et al., U.S. Pat. No. 4,537,726, disclose use of at least two adiabatic reaction stages which are linked in series. The quantities of oxygen fed to each reactor are limited in order to control process temperature.

Disadvantages attend each of the foregoing heat-control strategies. Use of small reactor diameters or multiple reactors increases equipment and engineering costs, and complicates process operation. When dealing with lower-boiling isocyanates, adding large volumes of inert gas (e.g., more than 50 volumes of inert gas per volume of oxygen) greatly increases the cost and expense of separating the desired product from the reactor effluent stream.

The improvement of the present invention permits partial or complete displacement of inert gas added to reactant streams for cooling, and use of single-stage reactor systems of conventional design. Accordingly, both capital and operating costs associated with isocyanate production can be greatly reduced. The improved process of the present invention is particularly suited for production of methyl isocyanate.

SUMMARY OF THE INVENTION

The present invention provides an improved process for preparing isocyanates of the formula R—NCO, wherein R is $C_{1-3}$ alkyl, by reacting a corresponding formamide of the formula R-NHCHO with oxygen or an oxygen-containing gas at a temperature from about 400° C. to about 800° C., in the presence of a silver catalyst, wherein the improvement comprises feeding water and formamide in vapor form to provide a reaction feed mixture having a mole ratio of water to formamide from about 0.1 to about 10.0.

DETAILED DESCRIPTION OF THE INVENTION

The present invention provides a process improvement for absorbing heat liberated in processes for producing isocyanates by oxidative dehydrogenation of formamides, as well as providing easier separation of the product isocyanate from the reaction mixture. U.S. Pat. No. 4,207,251 discloses a process for gas phase oxidation of N-monosubstituted formamides, wherein oxygen or an oxygen-containing gas such as air is added to the formamide and the resulting mixture passed over a copper and/or noble metal catalyst at a temperature from about 300° C. to 600° C. The catalysts employed can be copper and/or one or more metals selected from the group consisting of Ag, Au, Ru, Rh, Pd, Os, Ir, and Pt. Additional process details, such as reactants and process conditions, can be found in U.S. Pat. No. 4,201,251, the disclosure of which is incorporated herein by reference.

In the process of the present invention, silver catalysts are preferred, or combinations of silver and one or more of the other metals disclosed in U.S. Pat. No. 4,201,251. Preferably, the catalyst is in the form of crystals, or sputtered (vapor deposited) or ion plated on an inert support.

Oxidative dehydrogenation of formamides evolves a considerable amount of heat; the process improvement of the present invention provides a convenient and economic method of controlling process temperature. Unlike previously-disclosed methods, the present invention does not require addition of large quantities of inert gases to reaction mixtures or use of serial or parallel reactors of relatively small scale. Product losses in the recovery part of the process are thereby minimized.

According to the present invention, water, in the form of water vapor, is added to the formamide reactant in a mole ratio of water to formamide of from 0.1 to 10 prior to contact of the formamide with oxygen. For example, water can be added to the reactant stream immediately prior to its introduction to the reactor in which oxidative dehydrogenation is to take place. It is well-known that isocyanates react rapidly and violently with water in the liquid phase to form ureas; surprisingly, however, the isocyanates produced by the processes disclosed herein do not react with water in the vapor phase to an appreciable extent.

Immediately following contact with catalyst and formation of isocyanate, the reaction mixture containing water, unreacted formamide, and the low-boiling isocyanate can be introduced to partial condensation apparatus wherein water and unreacted formamide can be condensed and separated from the reactor effluent stream and then recycled to the reactor. The product isocyanates can then be further dried by contact with a molecular sieve, for example zeolite A3, prior to further purification and/or condensation or consumption in a subsequent process.

Reduction or elimination of large volumes of inert diluent gas greatly simplifies the task of condensing and separating products, resulting in higher overall yields at lower costs. Heretofore, so-called solvent borne isocyanate recovery processes or cryogenic condensation apparatus were employed (see, e.g., U.S. Pat. No. 4,207,251) to effect rapid separation of product isocyanate from byproduct water. Operation in accordance with the present invention permits use of simpler apparatus which provides separation of water and isocyanate streams without the need for cryogenic cooling.

Thus, in operating in accordance with the present invention, formamide and water are mixed in a molar ratio of water to formamide of from about 0.1 to 10, preferably from 0.5 to 2.0, and most preferably from 0.5 to 1.0, vaporized, mixed with oxygen or air, and then introduced to the reactor in the gas phase at a temperature from about 250° C. to about 350° C. Within the reactor, process temperatures are maintained from about 400° C. to about 800° C., preferably from about 450° C. to about 650° C. Reaction temperatures greater than about 800° C. should be avoided to minimize the occurrence of yield-reducing side reactions and product decomposition. Reaction temperatures from about 500° C. to about 650° C. are particularly preferred. For a given conversion, reaction temperature can be controlled by addition of inert gas or increasing the amount of added water.

Although the process disclosed herein can be run in batch or continuous modes, continuous modes are preferred. Single or multiple reactors, arranged in parallel or in series, can be employed, to which water, formamide, inert gas, or oxygen-containing gas can be added at various points in the process where staged reactors are employed. It is preferred, however, to employ a single reactor to reduce overall capital costs.

The absolute pressure at which the process of the present invention is conducted is not critical; generally, reaction pressures can vary from 100 to 1000 kPa. However, a reaction pressure of about 1 atmosphere (100 kPa) is preferred.

The most preferred application of the present process is in production of methyl isocyanate from monomethyl formamide. Methyl isocyanate is employed in the production of certain insecticides, particularly S-methyl-N-[(methylcarbamoyl)oxyl]thioacetimidate (methomyl).

EXAMPLES

The following examples illustrate particular aspects of the present invention. In the examples, product analyses are based upon area percent, determined by gas chromatography.

EXAMPLE 1

17.8 mL/hr of monomethyl formamide (MMF) was continuously vaporized and preheated to about 240° C. This was then mixed with 505 mL/min $N_2$ and 145 mL/min air (enough to convert 53.5% of the MMF) and sent to a reactor. The reactor was a 10 mm i.d. quartz tube containing 8.0 g of polycrystalline silver occupying a bed depth of about 2.5 cm. The reactor tube was equipped with a thermocouple to measure the temperature of the catalyst bed. The zone of the reactor containing catalyst was heated with an electric heater to a level sufficient to initiate reaction of MMF and $O_2$.

After initiating the reaction, power input to the heater was adjusted to compensate for heat lost to the surroundings, thereby approaching adiabatic operation. The average reactor temperature during this run was 554° C. The reactor product was analyzed by gas chromatography. There was very little unreacted oxygen leaving the reactor. The average yield of methyl isocyanate (MIC) was 92.8%, as measured by the following equation:

$$\text{MIC Yield} = \frac{[\text{MIC}]}{[\text{MIC}] + [\text{CO}_2]} \times 100.$$

EXAMPLE 2

The procedure of Example 1 was substantially repeated, except that a mixture of MMF and water having a mole ratio of 0.5 was employed. Since liquid feed rate was constant, enough oxygen was available to convert 62% of the MMF. The average reactor temperature was 555° C. and the average MIC yield at this higher conversion was 92.3%.

EXAMPLE 3

The procedure of Example 2 was substantially repeated, except that the mole ratio of MMF to water was 1.0. Sufficient oxygen was available to convert about 70% of the MMF. The average reactor temperature was 552° C. and the average MIC yield was 91.4% at this even higher conversion

EXAMPLES 4-9

The procedure of Example 2 was substantially repeated, except that the nitrogen flow was reduced to 404 mL/min. Enough oxygen was available to convert 62% of the MMF. Several runs were made under these feed conditions. Results are reported in Table 1, below.

TABLE 1

| Example | Reactor Temp. (°C.) | MIC yield (%) |
|---|---|---|
| 4 | 546 | 91.6 |
| 5 | 571 | 91.5 |
| 6 | 560 | 91.5 |
| 7 | 557 | 94.2 |
| 8 | 548 | 92.2 |
| 9 | 550 | 92.6 |

EXAMPLES 10-16

The procedure of Examples 4-9 was substantially repeated, except that the mode ratio of water to MMF was 1.0. Enough oxygen was available to convert about 70% of the MMF. Results are set forth in Table 2, below.

TABLE 2

| Example | Reactor Temp. (°C.) | MIC Yield (%) |
|---|---|---|
| 10 | 557 | 90.6 |
| 11 | 546 | 92.1 |
| 12 | 544 | 91.6 |
| 13 | 546 | 91.5 |
| 14 | 541 | 91.6 |
| 15 | 566 | 90.6 |
| 16 | 564 | 91.2 |

EXAMPLES 17-22

Examples 17-22 were conducted substantially as previously described, except that the flow rate of air was varied between 145 to 186 mL/min to give an MMF conversion of about 70% to 90%. The nitrogen flow rate was also varied. Liquid feed rate was 17.8 mL/hr of a 1:1 molar mixture of water and MMF. Results are set forth in Table 3, below.

TABLE 3

| Example | Reactor Temp. (°C.) | Flowrates (mL/min) Nitrogen | Flowrates (mL/min) Air | MIC Yield (%) |
|---|---|---|---|---|
| 17 | 561 | 405 | 145 | 94.1 |
| 18 | 586 | 205 | 145 | 91.0 |
| 19 | 599 | 205 | 166 | 91.7 |
| 20 | 607 | 205 | 176 | 91.8 |
| 21 | 615 | 205 | 186 | 91.2 |
| 22 | 632 | 205 | 186 | 88.0 |

What is claimed is:

1. An improved process for preparing isocyanates of the formula R—NCO, wherein R is $C_{1-3}$ alkyl, by reacting a corresponding formamide of the formula R-NHCHO with oxygen or an oxygen-containing gas at a temperature from about 400° C. to about 800° C., in the presence of a silver catalyst, wherein the improvement comprises feeding water and formamide in vapor form to provide a reaction feed mixture having a mole ratio of water to formamide from about 0.1 to about 10.0.

2. A process according to claim 1, wherein the temperature is from about 450° C. to about 650° C.

3. A process according to claim 2, wherein the mole ratio of water to formamide is from about 0.5 to about 2.0.

4. A process according to claim 3, wherein the formamide is monomethyl formamide.

5. A process according to claim 4, wherein the temperature is from about 500° C. to about 650° C.

6. A process according to claim 5, wherein the mole ratio of water to formamide is from about 0.5 to about 1.0.

* * * * *